United States Patent [19]

Bauman

[11] Patent Number: 4,821,713
[45] Date of Patent: Apr. 18, 1989

[54] RESUSCITATOR

[76] Inventor: Jack Bauman, 1677 San Onofre Dr., Pacific Palisades, Calif. 90272

[21] Appl. No.: 80,388

[22] Filed: Jul. 31, 1987

Related U.S. Application Data

[63] Continuation of Ser. No. 912,568, Sep. 29, 1986, abandoned, which is a continuation-in-part of Ser. No. 882,773, Jul. 7, 1986, abandoned.

[51] Int. Cl.$^4$ .............................................. A62B 7/00
[52] U.S. Cl. ......................... 128/205.13; 128/205.14; 128/205.23; 128/205.24
[58] Field of Search ...................... 128/203.23, 203.24, 128/205.11, 205.13, 205.17, 205.23, 205.24, 207.14, 727, 728, 203.11; 272/99; 116/266, 268, 270, 273, 335

[56] References Cited

U.S. PATENT DOCUMENTS

| | | | |
|---|---|---|---|
| 2,162,242 | 6/1939 | Branower | 128/205.23 |
| 3,017,881 | 1/1962 | Smith | 128/205.13 |
| 3,097,642 | 7/1963 | Russell | 128/205.13 |
| 3,366,133 | 1/1968 | Johannissen | 128/203.28 |
| 3,530,857 | 9/1970 | Miczka | 128/205.13 |
| 4,106,502 | 8/1978 | Wilson . | |
| 4,249,527 | 2/1981 | Ko et al. | 128/205.24 |

FOREIGN PATENT DOCUMENTS

| | | |
|---|---|---|
| 1491631 | 4/1970 | Fed. Rep. of Germany . |
| 869140 | 4/1941 | France ............................ 128/265.13 |
| 2063687 | 6/1981 | United Kingdom . |
| 2145335 | 3/1985 | United Kingdom . |

*Primary Examiner*—Edward M. Coven
*Assistant Examiner*—K. M. Reichle
*Attorney, Agent, or Firm*—William H. Haefliger

[57] ABSTRACT

A resuscitator comprises
(a) a manually collapsible air receptacle having an air inlet and discharge outlet,
(b) tubing sections extending in series and having an air inlet connectible in air passing relation with the receptacle inlet and discharge outlet, and an air outlet connectible in air passing relation with a mask to be placed against a patient's face,
(c) first and second valves positioned in at least one tubing section so that the first valve opens and passes air to the receptacle when the second valve is closed, and so that the second valve opens and passes air from the receptacle to the mask when the receptacle is squeezed and the first valve is closed, and
(d) an adjustable air bleed also being provided.

19 Claims, 4 Drawing Sheets

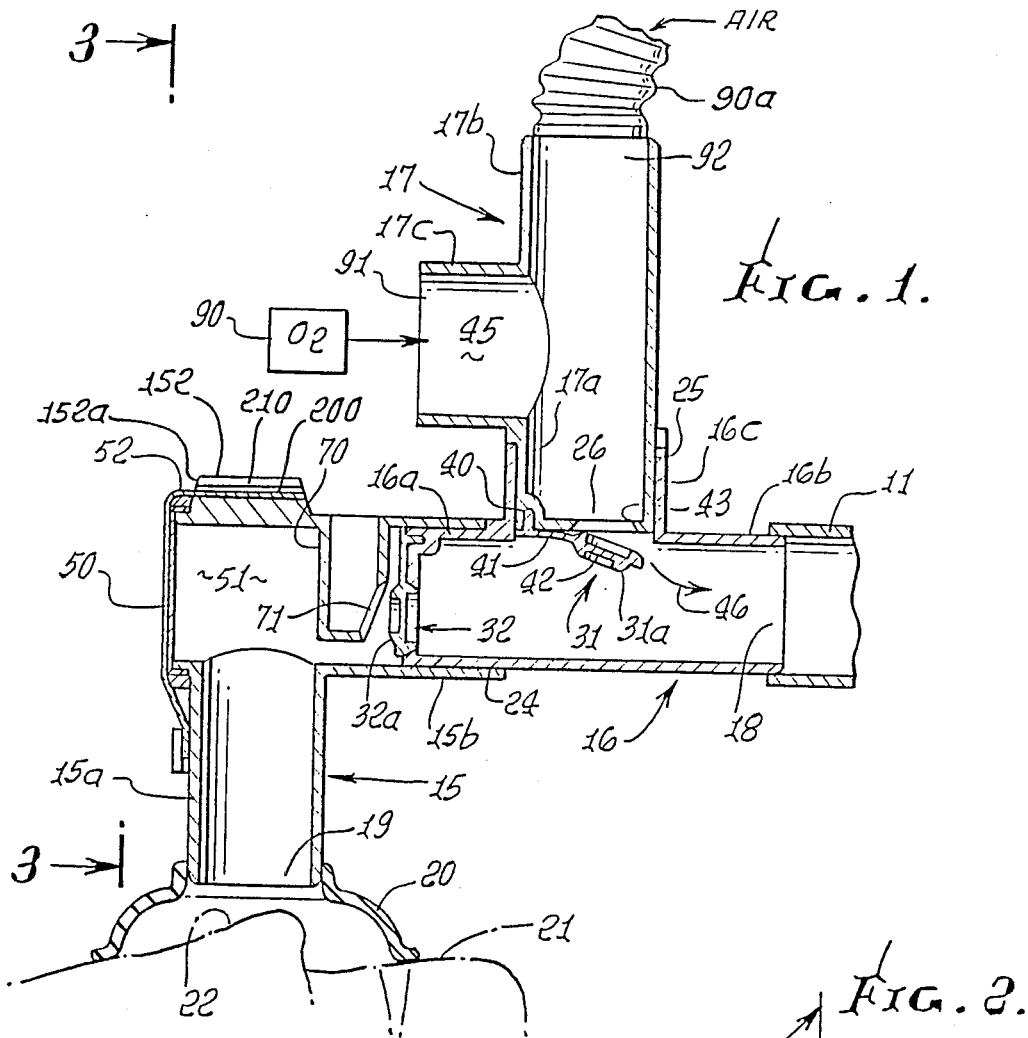
Fig. 1.
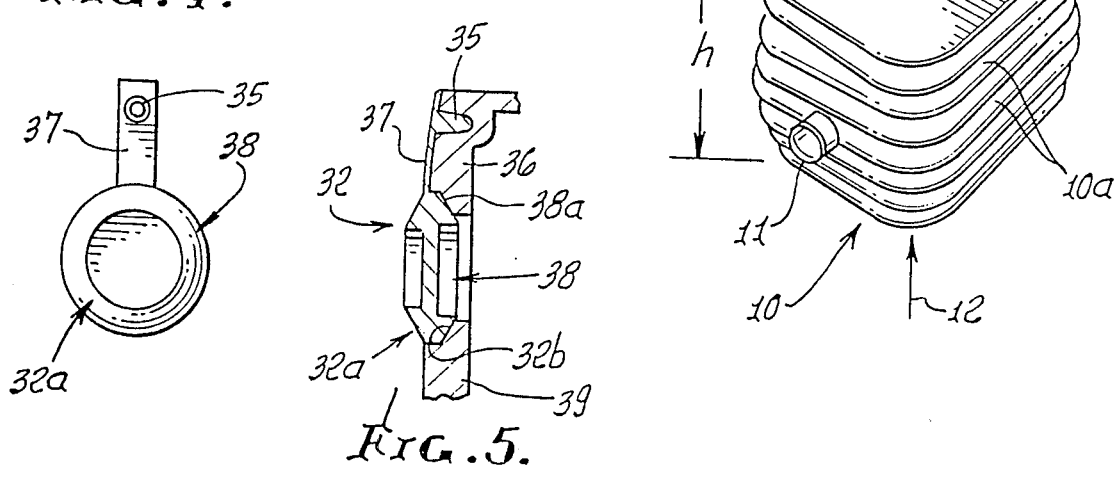
Fig. 2.
Fig. 4.
Fig. 5.

RESUSCITATOR

BACKGROUND OF THE INVENTION

This application is a continuation of Ser. No. 912,568, filed Sept. 29, 1986 which was a continuation-in-part of Ser. No. 882,773, filed July 7, 1986, both now abandoned. This invention relates generally to resuscitation of patients, as during heart attacks, shock, fainting, etc.; more particularly it concerns improved apparatus, characterized by high reliability, simplicity of construction, ease of use and safety against infection, and incorporation of multiple safety measures.

In the past, mouth-to-mouth resuscitation was believed to be necessary to provide required inhalation and exhalation of patients undergoing shock, heart attacks, etc.; however, the risk and danger of infection to the administrator of resuscitation is now recognized as serious, indeed critical, and to be avoided at all times. There is need for a simple, safe, and inexpensive resuscitation apparatus that is capable of easy manual use.

SUMMARY OF THE INVENTION

It is a major object of the invention to provide apparatus meeting the above need. Basically, the resuscitation apparatus of the invention comprises:

(a) manually collapsible air receptacle having an air inlet and discharge outlet, (b) tubing sections connected or extending in series and having air inlet means connectible in air passing relation with said receptacle inlet and discharge outlet, and an air outlet connectible in air passing relation with a mask to be placed against the patient's face, (c) first and second valves positioned in at least one tubing section so that the first valve opens and passes air to said receptacle when the second valve is closed, and so that the second valve opens and passes air from the receptacle to the mask when the receptacle is squeezed and the first valve is closed, (d) and air bleed means to control the amount of air passing from the receptacle to the mask irrespective of the extent of manual collapse of the receptacle.

As will be seen, the air receptacle typically comprises a bellow that is substantially completely hand-collapsible, so that a minimum size receptacle may be provided. Also, the tubing sections may be simplified in their construction and assembly, by use of first, second and third sections, two of which are T-shaped, and each having a side opening and end openings, the side opening of the second section registered with one end opening of third section. This also simplifies valve construction incorporating flaps in that the first flap valve controls the side opening of the second opening of the first section that is in registration with the second section.

Also, the air bleed means may be positioned compactly between the air receptacle and the first flap valve.

Another object is the provision of air bleed means having a stopper in the form of a manually adjustable rotor having different size vent openings therein, and selectively and successively registrable with the hollow interior of the tubing section. This enables ready adjustment of the apparatus to patient's with different breathing capacities, as will be seen.

Another object is the provision of a re-entrant duct extending into one tubing section and defining an air discharge port that is open to communicate with the air outlet when said second flap valve is closed, the second flap valve including a flap, and the air discharge port being closed by the flap of the second flap valve when said second flap valve is open. A cap may be provided to control escape of air from the re-entrant air discharge duct extending into one tubing section and movable to increase or decrease the effective size of said air discharge port.

A further object is the provision of an air pressure response indicator means carried by said section assembly to indicate the extent of pressure build-up between the second valve and said tubing section air outlet. That indicator means may include a plunger movable to variably register with color coding, and/or other indicia, to indicate plunger position.

Finally, an air pressure relief valve may be provided to prevent excess pressure build-up, as will be seen.

These and other objects and advantages of the invention, as well as the details of an illustrative embodiment, will be more fully understood from the following specification and drawings, in which:

DRAWING DESCRIPTION

FIG. 1 is a section showing interconnected tubing sections and associated flap valves;

FIG. 2 is a perspective view of a collapsible air receptacle connectible to the FIG. 1 tubing sections;

FIG. 4 is an enlarged frontal view of a valve flapper;

FIG. 5 is an enlarged crosssectional view of a portion of FIG. 1;

DETAILED DESCRIPTION

Figure 3:
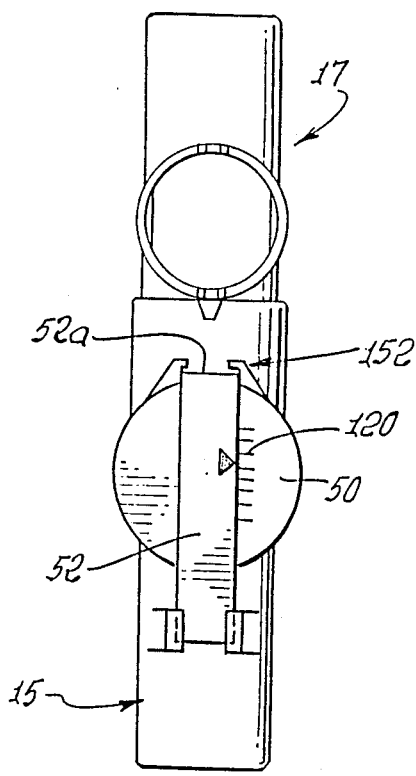
FIG. 3 is an end view on lines 3—3 of FIG. 1.

In FIGS. 1 and 2, a manually collapsible air receptacle 10 has an air inlet and discharge outlet 11 attached to a tubing assembly. The receptacle has a bellows-like configuration to be easily hand-held, and collapsed endwise, in a direction indicated by arrow 12. Note accordion-like pleasts 10a. The receptacle may have height "h", length "l", width "w" dimensions for convenient hand manipulation about as follows:

h=height 4 inches
l—about 4 inches
w—about 4 inches

Almost complete collapse of the receptacle can thereby be achieved.

The tubing assembly includes first, second and third tubular sections 15, 16 and 17, joined together in series, as shown. The assembly defines air inlet means, as at 18, connectible in air passing relation with the receptacle inlet and outlet 11, and an air inlet and outlet 19 connectible in air passing relation with a mask 20 configured to be placed against the patient's face 21, for supplying air to the patient as via his nose 22, for resuscitation. As shown, tubular section 15 is elbow shaped, and has tubular legs 15a and 15b; and sections 16 and 17 are alike and have tee shape. Their likeness enables reduction in molding costs, all sections consisting of molded plastic, for example. Section 16 has tubular legs 16a and 16b, and tubular stem 16c leg 16a having telescopic interfit at 24 with leg 15b. Section 17 has tubular legs 17a and 17b, and tubular stem 17c. Leg 17a has telescopic interfit at 25 with stem 16c. Thus, the side opening of second section 16 defined by stem 16c registers with the end opening 26 defined by leg 17a of third section 17. The telescopic interfits at 24 and 26 may be suitably bonded together to provide rigid connections.

Also provided are first and second flap valves generally indicated at 31 and 32, and positioned in at least one tubing section, so that the first flap valve 31 opens and passes intake air to the receptacle to inflate the same when the second flap valve is closed; and so that the second flap valve 32 opens while simultaneously closing opening 71, and passes air from the receptacle (upon squeezing thereof) to the mask 20 via outlet 19, and while flap valve 31 is closed. In this regard, the flap valves typically include normally closed flaps 31a and 32a, the latter illustrated in closed position in FIG. 1, and flap 31a illustrated in open position in that view. FIGS. 4 and 5 show flap 32a as having an anchor 35 penetrating and cemented to wall portion 36 of tubular section 16; a thin cantilevered flap spring arm 37, and disc 38 carried by the arm and annularly tapered at 38a to fit its annular seat 32b in wall 39, when the valve is closed. Valve flapper 31a is similarly configured, with parts 40, 41, 42 and 43 corresponding to parts 35, 37, 38 and 39. The flapper may consist of DELRIN plastic material, for example.

When the receptacle 10 is allowed to expand (after its forcible compression) inflating air enters side inlet 45 in section 17, opens flap valve 31, and flows to the receptacle as indicated by arrow 46. At this time, flap valve 32 is closed. When the receptacle is squeezed, flap valve 31 closes, and valve 32 opens while simultaneously closing 7, to pass air to outlet 19 and to the mask 20 to resuscitate the patient.

Figure 6:
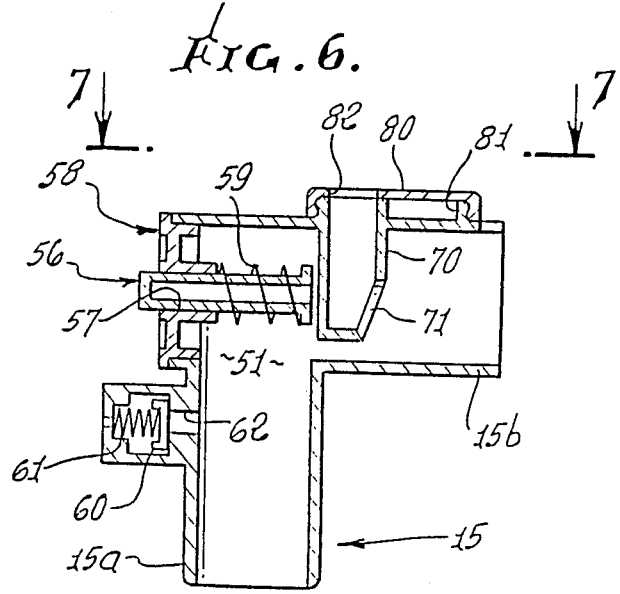
FIG. 6 is a section showing a modified tubing section.
Figure 7:
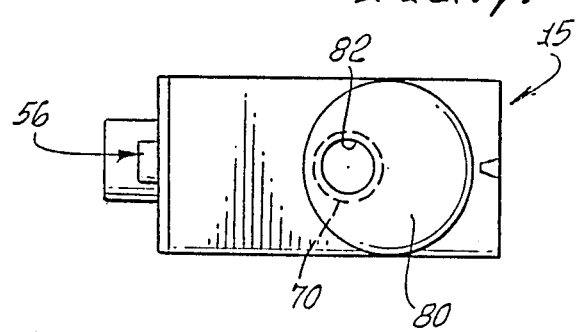
FIG. 7 is a top plan view taken on lines 7—7 of FIG. 6.

Air pressure indicator means may be carried by the tubular section assembly, to indicate the extent of pressure build-up between valve 32 and outlet 19. In the example shown in FIG. 1, the indicator comprises a movable pressure sensitive part in the form of a balloon membrane 50 exposed to the interior 51 of the elbow, and an indicator such as a slider 52 attached to the membrane. Increased pressure at 51 expands the membrane 50 to the left in FIG. 1, pushing the slider 52 to the left. Indicia at 200 on slider leg 52a variably register with edge 152a of retainer 152 as the leg moves leftwardly. A visible indication of pressure increase is thereby achieved, and indicia at 210 on the slider retainer 152 may indicate the degree of pressure increase, on a marker as the slider moves past the indicia 210. In FIGS. 6 and 7, the indicator takes the form of a plunger 56 slidable in a bore 57 formed by an insert 58 attached to the elbow. The extent of plunger travel to the left, resisted by a spring 59, indicates the extent of pressure build up at 51.

A safety valve may be provided to allow escape of excess pressure so that injury to the lungs of a patient, may be prevented. As shown, a check valve part 60 is urged by spring 61 to close outlet 62. Part 60 is pushed open by excess air pressure to allow air escape.

Also shown in FIG. 1 is a re-entrant duct 70 extending into leg 15b of section 15. It defines an air discharge port 71 that is open to communicate with the air outlet 19 upon exhalation by the patient, flap valve 32 then being closed against seat 32b. Exhaled lung air then escapes via duct 70. Alternately, port 71 is closed by flap 32a when the second flap valve 32 is open, to allow air to flow from the squeezed receptacle to the mask 20. Flap 32a thus performs two functions. Note that air may flow about the re-entrant duct in each position of the flap 32a, for minimum flow restriction.

In FIGS. 6 and 7, an enlarged cap 80 controls the effective size of discharge port 71, by controlling the escape of air from the re-entrant duct 70. To this end, the cap 80 fits annularly over an annular neck 81 on the leg 16b; and the cap has an opening 82 thereon that variably registers with the duct 70 as the cap is rotated on the enlarged neck. This serves as a control for air escape upon natural exhalation by the patient, so that positive and expiratory pressure (PEEP) may be achieved if desired.

In FIG. 1, a source of oxygen 90 may be connected with the inlet 45, so that supplied $O_2$ enters via inlet 91 for flow to the receptacle and optional reservoir tubing 90a, and later to the patient. More particularly, a reservoir tubing 90a which has a first opened end connectable to tube section 17b and a second end (not shown) spaced from this coupling. The remote end of the oxygen reservoir is preferably an open end to allow free flow of air thereinto when necessary. When valve 31 is closed, for example when collapsible receptacle 10 is being manually compressed to ventilate the patient, the oxygen flow into inlet 45 will nevertheless continue due to the continuous flow of oxygen from the oxygen source 90. Because valve 31 is closed, the oxygen fed into inlet 45 will tend to flow throughout tubular section 17 and up into reservoir 90a. Then, when the collapsible reservoir 10 is released and valve 32 closed, valve 31 will again open and the oxygen which has begun to fill the oxygen reservoir 90a will be drawn down into tube section 16 and into the collapsible reservoir 10. Thus, the provision of an extension tube 90a to collect oxygen delivered to tubular section 17 while valve 31 is closed constitutes an oxygen reservoir and enables collected oxygen to be fed to the collapsible reservoir when it is refilled. An oxygen flow rate of as little as 8 liters per minute will supply 100% oxygen to the patient.

Figure 8:
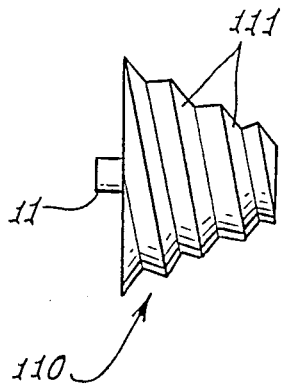
FIG. 8 is a view showing an alternative collapsible receptacle.
Figure 9:
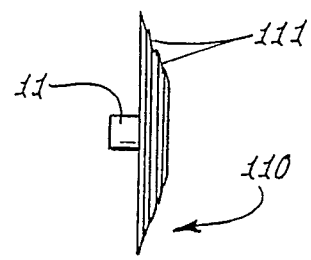
FIG. 9 shows that receptacle in collapsed condition.

FIG. 8 shows an alternative conical shaped receptacle 110, for air or oxygen, for use in place of receptacle 10. Its pleats 111 allow its complete endwise collapse, manually, as shown in FIG. 9. Thus maximal air discharge is achieved; and also high compactness is achieved for storage, as in a user's pocket.

Figure 10:
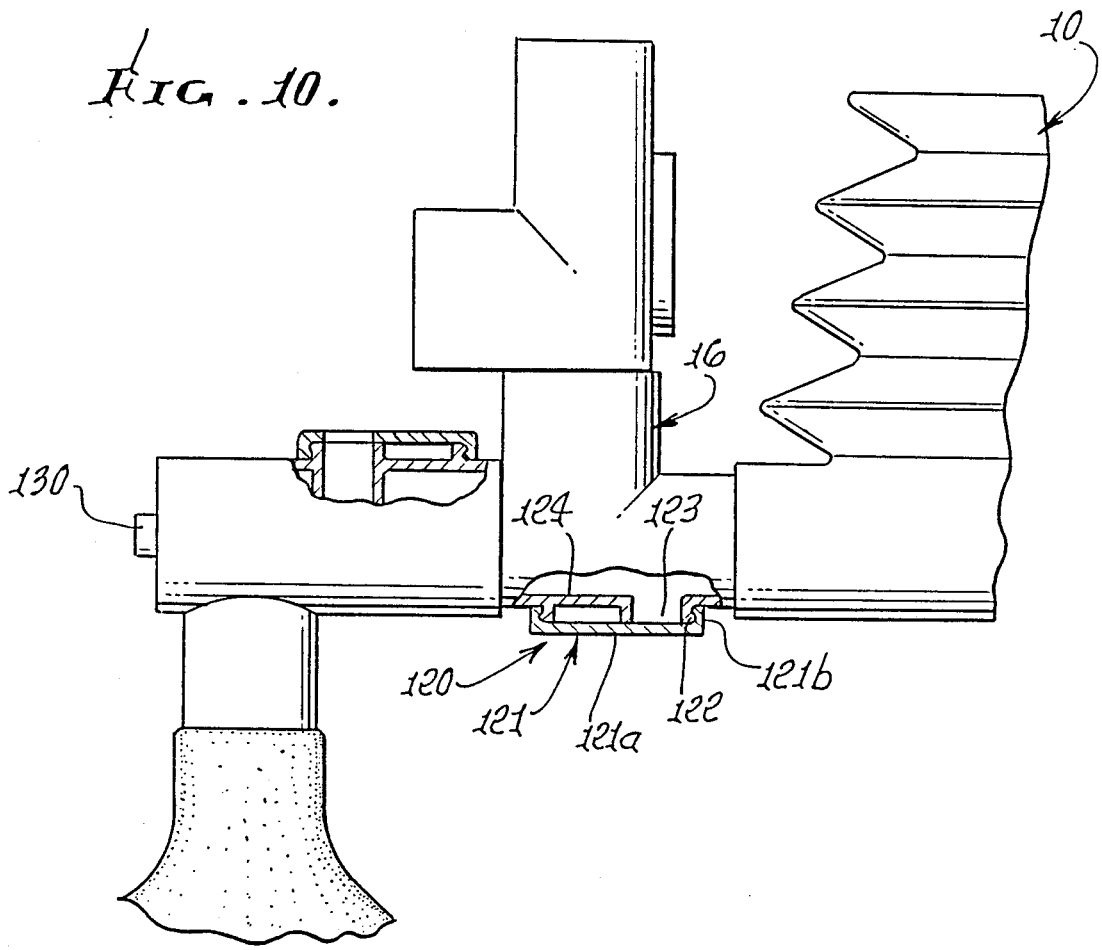
FIG. 10 is fragmentary side elevation showing provision of air bleed means.

In FIG. 10 the elements are as previously described, excepting as follows: the second tubular section 16 carries air bleed means, generally indicated at 120, for controlling the amount of air passing to the mask, irrespective of the amount of manual collapse of the receptacle 10. The functioning is such that the user may repeatedly collapse and expand the receptacle 10 without exerting excessive air pressure on the lungs of the patient.

For this purpose, the air bleed means includes manually adjustable air vent structure, as for example, a stopper having multiple selected positions associated with different valve openings past or through the stopper. FIGS. 11a–11d, show the stopper in the form of a rotor or rotatable cap 121 having an end wall 121a and a skirt 121b grippingly interfitting an annular lip 122 on the section 16. Lip 122 surrounds a smaller vent opening 123 through wall 124 of section 16.

Figure 11:
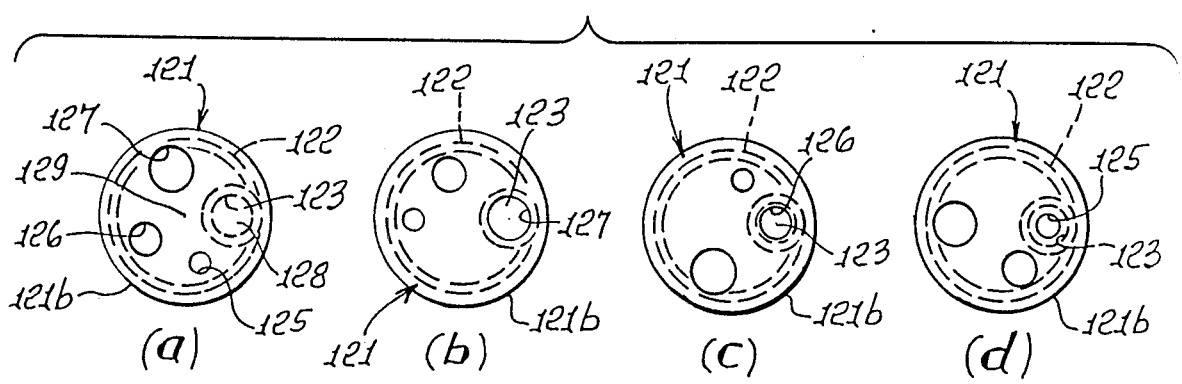
FIGS. 11a–11d are views of an air bleed rotor in different selected positions.

The end wall 121a has different sized vent openings 125–127 therein, spaced about axis 129 of rotation, and of selectively larger size to be selectively and individually brought into registration with vent opening 123. Region 128 of the rotor has no vent opening therein, and as shown in rotor position of FIG. 11a, it covers the vent 123 in wall 124. Such position would be used when maximum air flow and pressure to the patient is desired. In the rotor position of FIG. 11b, minimum air flow to the patient (such as a baby) is desired, and maximum venting via 123 and 127 is effected (some air of course passing to the patient via the flap valves, as described previously). In FIGS. 11c and 11d, intermediate positions of the rotor, lesser by-pass venting occurs, as for children, smaller adults, etc. Vent openings may be covered by an elastomeric flap to function as check valves, if desired, the construction being like that of FIGS. 4 and 5.

Figure 12:
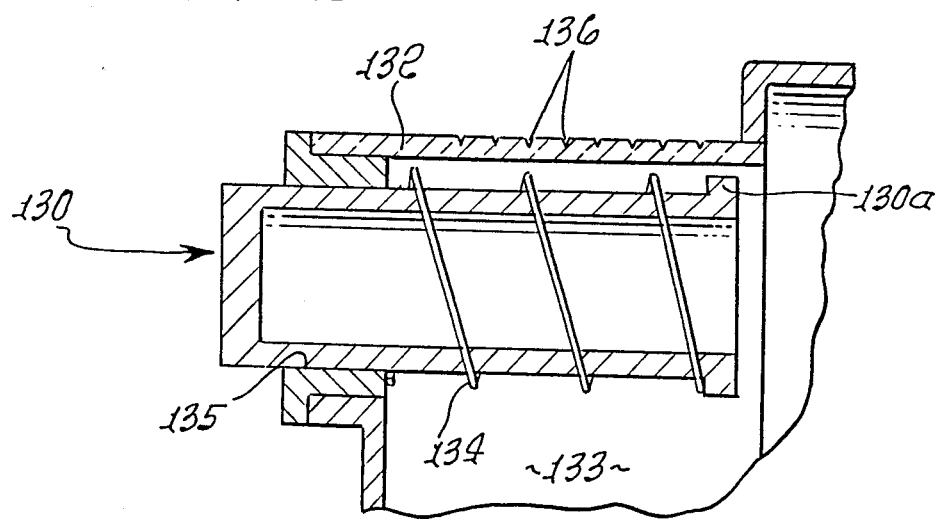
FIGS. 12 and 13 are fragmentary side elevations showing pressure build-up sensing structures.

FIG. 12 shows a plunger 130 corresponding to plunger 56 in FIG. 6, except that plunger 130 is of larger diameter, so that its end flange 130a (or other marker thereon) extends or moves closely adjacent to a transparent wall 132 of a tubular section. The latter carries indicia with which the flange 130a is variably registrable as the plunger moves endwise (i.e. pressure build-up in interior 133, and the plunger moves leftwardly as resisted by light spring 134). Guide bore 135 is provided for guiding plunger movement.

The indicia referred to may take the form of markings 136 on the transparent wall, as shown, so that as the plunger moves, the registration of the flange 130a with different markings is indicating changes in pressure build-up. Spring 134 returns the plunger rightwardly as pressure drops in space 133.

Figure 13:
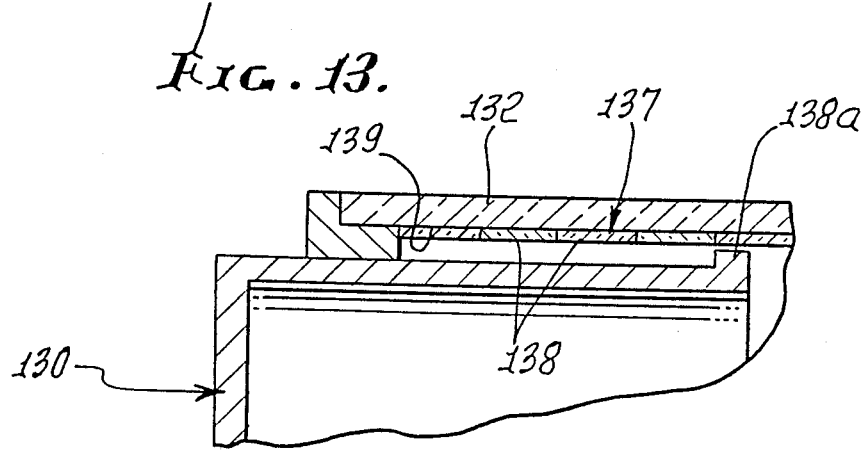

FIG. 13 shows the provision of color coded indicator means 137. It is in the form of a lengthwise color coded semi-transparent sleeve 138 fitting against the bore 139 defined by wall 132. Thus, as flange 138a moves left and right, it variably registers with the different color codes on the sleeve, all of which is visible through transparent wall 132.

I claim:

1. A resuscitator for ventilating a patient comprising:
   a ventilator mask means for sealingly surrounding the patient's mouth and nose;
   a gas flow manifold having first, second, and third gas flow passage means for delivering ventilating gas from a source of ventilating gas to said mask means;
   means for operatively coupling said third gas flow passage means to said mask means;
   a manually collapsible gas receptacle;
   means for operatively coupling said manually collapsible gas receptacle to said first gas flow passage means;
   said second gas flow passage means being in flow communication with a source of ventilating gas;
   said first gas flow passage means being operatively coupled to said third gas flow passage means and said second gas flow passage means being operatively coupled to said first gas flow passage means;
   first one-way flow valve means mounted intermediate said second and first gas flow passage means for preventing flow from said first gas flow passage means to said second gas flow passage means and allowoing flow from said second gas flow passage means to said first gas flow passage means;
   second one-way flow valve means mounted intermediate said first and third gas flow passage means for preventing flow from said third gas flow passage means to said first gas flow passage means and allowing flow from said first gas flow passage means to said third gas flow passage means;
   said first one-way flow valve means and said second one-way flow valve means being mounted so that when said manually collapsible gas receptacle is collapsed, said first one-way flow valve means prevents flow from said first gas flow passage means to said second gas flow passage means and said second one-way flow valve means allows from said first gas flow passage means to said third gas flow passage means and, when said manually collapsible gas receptacle expands, said first one-way flow valve means allows flow from said second gas flow passage means to said first gas flow passage means and said second one-way flow valve means prevents flow from said third gas flow passage means to said first gas flow passage means;
   said third gas flow passage means including gas outlet means and means for closing said gas outlet means when said second one-way flow valve means allows flow from said first to said third gas flow passage means;
   said gas flow manifold further including means for detecting air pressure within said third gas flow passage means and for defining a portion of a wall of said third gas flow passage means; and
   a wall of said third gas flow passage means having means for indicating the pressure detected by said air pressure detecting means.

2. A resuscitator as in claim 1, wherein said first one-way flow valve means and said second one-way flow valve means each comprise a flap valve.

3. A resuscitator as in claim 1, wherein said gas outlet means comprises an aperture through a wall of said third gas flow passage means, said second one-way flow valve means comprising a flap valve, said flap valve being mounted adjacent said aperture and defining said means for closing such that when the second one-way flow valve allows flow from said first to said third gas flow passage means, said flap valve closes said aperture of said gas outlet means.

4. A resuscitator as in claim 3, further including air bleed means mounted to a wall of said first flow passage means having a manually adjustable air vent means for controlling the amount of air passing from the collapsible receptacle through said first flow passage means to said third flow passage means.

5. A resuscitator as in claim 3, further including cap means mounted to said aperture for controlling the size of said aperture.

6. A resuscitator as in claim 1, wherein said receptacle comprises a bellows-element having folds for allowing said bellows to substantially completely collapse.

7. A resuscitator as in claim 1, wherein said means for detecting air pressure and defining a portion of a wall of said third gas flow passage means comprises a movable pressure sensitive balloon membrane defining a portion of a wall of said thid gas flow passage means which expands when the pressure in said third gas flow passage means increases, and wherein a slider element is attached to said balloon membrane and is slidably coupled to a wall of said third gas flow passage so as to slide relative thereto when said balloon membrane expands, and said indicating means includes indicia on said wall of said third gas flow passage to which said slider element is slidably coupled whereby movement of said slider element relative to the indicia on said wall indicates the pressure detected by said balloon membrane.

8. A resuscitator as in claim 1, wherein a bore is defined in a wall of said third gas flow passage means, said means for detecting air pressure and for defining a portion of a wall of said third gas flow passage comprising a plunger slidaby mounted in said bore, said plunger having a flange defined thereon, a spring means mounted intermediate said flange of said plunger and said wall of said third gas flow passage so as to limit movement of said plunger relative to said wall of said third gas flow passage means, at least a portion of a wall of said third gas flow passage means being transparent such that movement of said plunger relative to said transparent wall can be seen exteriorly of said transparent wall and wherein said indicating means includes indicia on said transparent wall whereby movement of said plunger relative to the indicia on said transparent wall indicates the pressure detected by said plunger.

9. A resuscitator as in claim 8, wherein said indicia comprises a series of numbers indicating the pressure detected by said plunger.

10. A resuscitator as in claim 8, wherein said indicia comprise a plurality of colored translucent segments for indicating the pressure detected by said plunger.

11. A gas flow manifold for a resuscitator for ventilating a patient comprising:
a housing;
first, second, and third gas flow passage means defined within said housing for delivering ventilating gas from a source of ventilating gas to the patient;
means for operatively coupling said third gas flow passage means to a ventilator mask for sealingly surrounding the patient's mouth and nose;
means for operatively coupling a manually collapsible gas receptacle to said first gas flow passage means;
said second gas flow passage means being in flow communication with a source of ventilating gas;
said first gas flow passage means being operatively coupled to said third gas flow passage means and said second gas flow passage means being operatively coupled to said third gas flow passage means;
first one-way flow valve means mounted intermediate said second and first gas flow passage means for preventing flow from said first gas flow pasage means to said second gas flow passage means and allowoing flow from said second gas flow passage means to said first gas flow passage means;
second one-way flow valve means mounted intermediate said first and third gas flow passage means for preventing flow from said third gas flow passage means to said first gas flow passage means and allowing flow from said gas flow passage means to said third gas flow passage means;
said first one-way flow valve means and said second one-way flow valve means being mounted so that when said manually collapsible gas receptacle is collapsed, said first one-way flow valve means prevents flow from said first gas flow passage means to said second gas flow passage means and said second one-way flow valve means allows flow from said first gas flow passage means to said third gas flow passage means and, when said manually collapsible gas receptacle expands, said first one-way flow valve means allows flow from said second gas flow passage means to said first gas flow passage means and said second one-way flow valve means prevents flow from said third gas flow passage means to said first gas flow passage means;
said third gas flow passage means including gas outlet means and means for closing said gas outlet means when said second one-way flow valve means allows flow from said first to said third gas flow passage means;
said gas flow manifold further including means for detecting air pressure within said third gas flow passage means and for defining a portion of a wall of said third gas flow passage means; and
a wall of said third gas flow passage means having means for indicating the pressure detected by said air pressure detecting means.

12. A resuscitator as in claim 11, wherein said first one-way flow valve means and said second one-way flow valve means each comprise a flap valve.

13. A resuscitator as in claim 11, wherein said gas outlet means comprises an aperture defined through a wall of said third gas flow passage means, said second one-way flow valve flow means comprising a flap valve, said flap valve being mounted adjacent said aperture and defining said means for closing such that when said second one-way flow valve allows flow from said first to said third gas flow passage means, said flap valve closes said aperture of said gas outlet means.

14. A resuscitator as in claim 13, further including air bleed means mounted to a wall of said first flow passage means having a manually adjustable air vent means for controlling the amount of air passing from the collapsible receptacle through said first flow passage means to said third flow passage means.

15. A resuscitator as in claim 13, further including cap means mounted to said aperture for controlling the size of said aperture.

16. A resuscitator as in claim 11, wherein said means for detecting air presusre and defining a portion of a wall of said third gas flow passage means comprises a movable pressure sensitive balloon membrane defining a portion of a wall of said third gas flow passage means which expends when the pressure in said third gas flow passage means increases, and wherein a slider element is attached to said balloon membrane and is slidably coupled to a wall of said third gas flow passage so as to slide relative thereto when said balloon membrane expands, and said indicating means includes indicia on said wall of said third gas flow passage to which said slider element is slidably coupled whereby movment of said slider element relative to the indicia on said wall indicates the pressure detected by said balloon membrane.

17. A resuscitator as in claim 11, wherein a bore is defined in a wall of said third gas flow passage means, said means for detecting air pressure and for defining a portion of a wall of said third gas flow passage comprising a plunger slidably mounted in said bore, , said plunger having a flange defined thereon, a spring means mounted intermediate said flange of said plunger and said wall of said third gas flow passage so as to limit movement of said plunger relative to said wall of said third gas flow passage means, at least a portion of a wall of said third gas flow passage means being transparent such that movement of said plunger relative to said transparent wall can be seen exteriorly of said transparent wall and wherein said indicating means includes indicia on said transparent wall whereby movement of siad plunger relative to the indica on said transparent wall indicates the pressure detected by said plunger.

18. A resuscitator as in claim 17, wherein said indicia comprises a series of numbers indicating the pressure detected by said plunger.

19. A resuscitator as in claim 17, wherein said indicia comprise a pluralilty of colored translucent segments for indicating the pressure detected by said plunger.

* * * * *